(12) United States Patent
Fu et al.

(10) Patent No.: US 7,160,916 B2
(45) Date of Patent: Jan. 9, 2007

(54) METHOD OF INCREASING BONE DENSITY OR TREATING OSTEOPOROSIS

(75) Inventors: Wen-Mei Fu, Taipei (TW); Chih-Hsin Tang, Miaoli (TW); Rong-Sen Yang, Taipei (TW); Che-Ming Teng, Taipei (TW); Sheng-Chu Kuo, Taichung (TW); Fang-Yu Lee, Tachia Taichung (TW)

(73) Assignee: Yung Shin Pharmaceutical Ind. Co., Ltd., Taipei (TW)

( * ) Notice: Subject to any disclaimer, the term of this patent is extended or adjusted under 35 U.S.C. 154(b) by 174 days.

(21) Appl. No.: 10/932,323

(22) Filed: Sep. 1, 2004

(65) Prior Publication Data

US 2005/0131048 A1   Jun. 16, 2005

Related U.S. Application Data

(60) Provisional application No. 60/499,696, filed on Sep. 3, 2003.

(51) Int. Cl.
*A61K 31/416* (2006.01)
*A61K 31/415* (2006.01)
*A61K 31/38* (2006.01)
*A61K 31/34* (2006.01)
*A61K 31/40* (2006.01)

(52) U.S. Cl. ............ 514/406; 514/443; 514/469; 514/471; 514/412; 514/427; 514/405

(58) Field of Classification Search ............ 514/406, 514/443, 469, 471, 412, 427, 405
See application file for complete search history.

(56) References Cited

U.S. PATENT DOCUMENTS

| 5,574,168 | A * | 11/1996 | Kuo et al. ............ 548/360.5 |
| 6,162,819 | A | 12/2000 | Schindler et al. |
| 7,049,334 | B1 * | 5/2006 | Fu et al. ............ 514/406 |
| 2003/0072748 | A1 | 4/2003 | Black et al. |
| 2003/0105149 | A1 | 6/2003 | Fu et al. |
| 2005/0187276 | A1 * | 8/2005 | Park et al. ............ 514/396 |

FOREIGN PATENT DOCUMENTS

| WO | WO 98/09961 | 8/1997 |
| WO | WO 99/23076 | 5/1999 |
| WO | WO 01/53268 | 7/2001 |
| WO | WO 03/035625 | 5/2003 |
| WO | WO 03/064397 | 8/2003 |

OTHER PUBLICATIONS

Friebe et al., "Potentiates Nitric Oxide- and Carbon Monoxide-Induced Cyclic GMP Effects in Human Platelets", Molecular Pharmacology, 54:962-967, 1998.
Ko et al., "YC-1, a Novel Activator of Platelet Guanylate Cyclase" Blood, vol. 84, No. 12, pp. 4226-4233, 1994.

* cited by examiner

*Primary Examiner*—Brian Kwon
(74) *Attorney, Agent, or Firm*—Fish & Richardson P.C.

(57) ABSTRACT

This invention features a method for enhancing bone growth or inhibiting bone resorption. The method includes administering to a subject in need thereof a compound of the following formula:

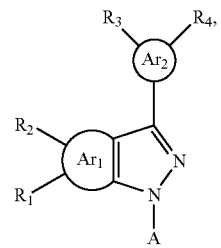

A is H, R, or

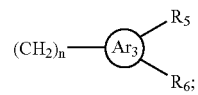

each of $Ar_1$, $Ar_2$, and $Ar_3$, independently, is phenyl, thienyl, furyl, or pyrrolyl; each of $R_1$, $R_2$, $R_3$, $R_4$, $R_5$, and $R_6$, independently, is H, halogen, R, C(O)OH, C(O)OR, C(O)SH, C(O)SR, C(O)NH$_2$, C(O)NHR, C(O)NRR', ROH, ROR', RSH, RSR', NHR, NRR', RNHR', or RNR'R"; or $R_1$ and $R_2$ together, $R_3$ and $R_4$ together, or $R_5$ and $R_6$ together are ORO; wherein each of R, R', and R", independently, is $C_1$–$C_6$ alkyl; and n is 1, 2, or 3.

10 Claims, No Drawings

METHOD OF INCREASING BONE DENSITY OR TREATING OSTEOPOROSIS

RELATED APPLICATIONS

This application claims priority to U.S. provisional application No. 60/499,696, filed on Sep. 3, 2003, the content of which is incorporated herein by reference.

BACKGROUND

Bone is a complex tissue, which continuously undergoes renewal and repair, a process termed "bone remodeling." Two major cell types responsible for bone remodeling are osteoclasts, which resorb bone, and osteoblasts, which form new bone. Bone remodeling is regulated by several systemic hormones (e.g., parathyroid hormone, 1,25-dihydroxybitamin $D_3$, sex hormones and calcitonin), and local factors (e.g., nitric oxide, prostaglandins, growth factors and cytokines). When resorption and formation of bone are not coordinated and bone breakdown overtakes bone building, osteoporosis results. Osteoporosis is also caused by other conditions, such as hormonal imbalances, diseases, or medications (e.g. corticosteroids or anti-epileptic agents).

Compounds that modulate bone remodeling process, either by inhibiting bone resorption or activating bone formation, have the potential for enhancing bone growth, and can be used to treat osteoporosis.

SUMMARY OF THE INVENTION

The invention is based on a discovery that a fused pyrazolyl compound, unexpectedly, inhibits bone resorption and enhances bone growth.

An aspect of this invention relates to a method for enhancing bone growth or inhibiting bone resorption. The method includes administering to a subject in need thereof an effective amount of a fused pyrazolyl compound of the following formula:

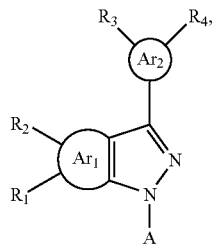

wherein A is H, R, or

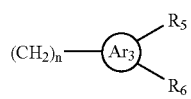

(referred to as "$(CH_2)_nAr_3(R_5)(R_6)$" hereinafter);

each of $Ar_1$, $Ar_2$, and $Ar_3$, independently, is phenyl, thienyl, furyl, or pyrrolyl; each of $R_1$, $R_2$, $R_3$, $R_4$, $R_5$, and $R_6$, independently, is H, halogen, R, C(O)OH, C(O)OR, C(O)SH, C(O)SR, C(O)NH$_2$, C(O)NHR, C(O)NRR', ROH, ROR', RSH, RSR', NHR, NRR', RNHR'; or RNR'R", or $R_1$ and $R_2$ together, $R_3$ and $R_4$ together, or $R_5$ and $R_6$ together are ORO. Each of R, R', and R", independently is $C_1$–$C_6$ alkyl; and n is 1, 2, or 3.

Referring to the above formula, a subset of the compounds of formula (I) feature by that A is $(CH_2)_nAr_3(R_5)$ ($R_6$). In one embodiment, $Ar_1$ is phenyl, and $R_1$ and $R_2$ are substituted at positions 4 and 5 of phenyl, respectively. In another embodiment, Ar2 is 5'-furyl, and one of $R_3$ and $R_4$ is substituted at position 2 of 5'-furyl. In still another embodiment, $Ar_3$ is phenyl and n is 1.

Another subset of the compounds feature by that A is H. In one embodiment, $Ar_1$ is phenyl, and $R_1$ and $R_2$ are substituted at positions 4 and 5 of phenyl, respectively. In another embodiment, $Ar_2$ is 5'-furyl, and one of $R_3$ and $R_4$ is substituted at position 2 of 5'-furyl.

Still another subset of the compounds feature by that $Ar_1$ is phenyl or $Ar_2$ is 5'-furyl.

The term "alkyl" refers to a straight or branched hydrocarbon, containing 1–10 carbon atoms. Examples of alkyl groups include, but are not limited to, methyl, methylene, ethyl, ethylene, n-propyl, i-propyl, n-butyl, i-butyl, and t-butyl. The alkyl may optionally substituted. Examples of a substituent include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkenyl, alkynyl, alkyloxy, aryl, heteroaryl, cyclyl, and heterocyclyl, in which the alkenyl, alkynyl, alkyloxy, aryl, heteroaryl cyclyl, and heterocyclyl may be further substituted.

The above-described fused pyrazolyl compound includes its salts and prodrugs, if applicable. Such salts, for example, can be formed between a negatively charged substituent (e.g., carboxylate) on a fused pyrazolyl compound and a cation. Suitable cations include, but are not limited to, sodium ion, potassium ion, magnesium ion, calcium ion, and an ammonium cation such as teteramethylammonium ion. Likewise, a positively charged substituent (e.g., amino) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing fused pyrazolyl compounds described above.

Another aspect of this invention relates to a method of treating osteoporosis. The method includes administering to a subject in need thereof an effective amount of the fused pyrazolyl compound described above.

Set forth below is an example of a fused pyrazolyl compound that can be used to practice the method of this invention:

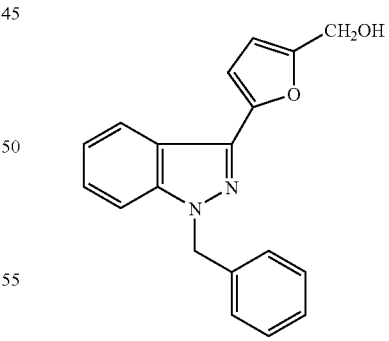

Indazole 1

Also within the scope of this invention is the use of the above-described compound for the manufacture of a medicament for enhancing bone growth, inhibiting bone resorption, or treating osteoporosis.

The details of many embodiments of the invention are set forth in the description below. Other features, objects, and advantages of the invention will be apparent from the description and the claims.

DETAILED DESCRIPTION OF THE INVENTION

A fused pyrazolyl compound used to practice the method of this invention can be prepared by procedures well known to a skilled person in the art (see, e.g., U.S. Pat. No. 5,574,168). They include the synthetic route that follows: An aryl aryl ketone is first prepared by coupling an arylcarbonyl chloride with another aryl compound. Either aryl compound is optionally mono- or multi-substituted. The ketone then reacts with an arylalkylhydrazine, the aryl group of which is also optionally mono- or multi-substituted, to form a hydrazone containing three aryl groups. The hydrazone group is transformed into a fused pyrazolyl core via an alkylene linker, another aryl group is fused at 4-C and 5-C of the pyrazolyl core, and the third aryl group is directly connected to 3-C of the pyrazolyl core. Derivatives of the fused pyrazolyl compound may be obtained by modifying the substituents on any of the aryl groups.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the fused pyrazolyl compound. In addition, various synthetic steps may be performed in an alternate sequence or order to give the desired compounds. Synthetic chemistry transformations and protecting group methodologies (protection and deprotection) useful in synthesizing applicable fused pyrazolyl compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A fused pyrazolyl compound thus synthesized can be further purified by a method such as column chromatography, high pressure liquid chromatography, or recrystallization.

One aspect of this invention is a method for enhancing bone growth or inhibiting bone resorption. Thus, the method includes, but is not limited to, treating osteoporosis, bone fractures, short stature, failed arthrodesis, dyschondroplasia, achondroplasia, or congenital pseudoarthrosis. Examples of "osteoporosis" include, but are not limited to, postmenopausal osteoporosis, senile osteoporosis, idiopathic osteoporosis, corticosteroid-induced osteoporosis, and Vitamin D-deficiency-related osteoporosis. Examples of "bone fractures" include, but are not limited to, nonunion, delayed union, and pathological fracture. The method includes administering to a subject in need thereof an effective amount of one or more fused pyrazolyl compounds and a pharmaceutically acceptable carrier. As used herein, the term "treating" refers to alleviating, relieving, remedying or ameliorating diseases associated with inadequate bone growth, such as osteoporosis. "An effective amount" is defined as the amount of the fused pyrazolyl compound which, upon administration to a subject in need thereof, is required to confer therapeutic effect on the subject. An effective amount of the frised pyrazolyl compound can range from about 0.01 mg/kg to about 300 mg/kg. The effective amount will vary, as recognized by those skilled in the art, depending on route of administration, excipient usage, and the possibility of co-usage with other agents for enhancing bone growth, or with other agents for treating osteoporosis.

To practice the method of the present invention, a composition containing a fused pyrazolyl compound and a pharmaceutically acceptable carrier can be administered orally, parenterally, by inhalation spray or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

A carrier in a pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the fused pyrazolyl compound, or one or more solubilizing agents, can be utilized as pharmaceutical excipients for delivery of the fused pyrazolyl compound. Examples of other carriers include colloidal silicon dioxide, magnesium stearate, cellulose, sodium lauryl sulfate, and D&C Yellow #10.

A suitable in vitro assay can be used to preliminarily evaluate a fused pyrazolyl compound's ability to increase the formation of bone nodules. In vivo screening can also be performed by following procedures well known in the art. See the specific examples below.

Without further elaboration, it is believed that the above description has adequately enabled the present invention. The following specific embodiments are, therefore, to be construed as merely illustrative, and not limitative of the remainder of the disclosure in any way whatsoever. All of the publications, including patents, cited herein are hereby incorporated by reference in their entirety.

Chemical Synthesis

Calcium borohydride was first prepared by stirring anhydrous calcium chloride (88.8 mg, 0.8 mmole) with sodium borohydride (60 mg, 1.6 mmole) in anhydrous THF (20 mL) for 4 hrs. A 30 mL THF solution containing 88.0 mg 1-benzyl-3-(5'-methoxycarbonyl-2'-furyl)-indazole (0.27 mmole) was then added dropwise to the calcium borohydride solution at 30±2° C. The mixture was heated under reflux for 6 hrs, cooled, quenched into crushed ice, placed at a reduced pressure to remove THF, and filtered to obtain a solid product. The solid was extracted with dichloromethane. The extract was concentrated to 50 mL and a solid precipitated after petroleum ether was added. The precipitate was collected and purified by column chromatography (silica gel-benzene) to obtain 70.0 mg 1-benzyl-3-(5'-hydroxymethyl-2'-furyl)-indazole at a yield of 87%. This compound is referred to as "Indazole 1" below.

mp: 108–109° C.

MS (%), m/z: 304 ($M^+$).

IR (KBr) $\lambda_{max}$: 3350 $cm^{-1}$ (—OH).

$^1$H-NMR (DMSO-$d_6$, 200 MHz) δ: 4.51 (2H, d, J=5.5 Hz, —$CH_2O$—), 5.31 (1H, t, J=5.5 Hz, —OH), 5.70 (2H, s, =$NCH_2$—), 6.48 (1H, d, J=3.4 Hz, H-4'), 6.97 (1H, d, J=3.4 Hz, H-3'), 7.21–7.31 (6H, m, H-5, phenyl), 7.45 (1H, t, J=8.2 Hz, H-6), 7.75 (1H, dd, J=8.2, 1.8 Hz, H-7), 8.12 (1H. dd, J=8.2. 1.0 Hz. C4-H).

Biological Assays

Methods

Primary osteoblast cultures: Primary osteoblast cells were prepared from calvaria of 18-day-old fetal Sprague-Dawley (SD) rats according to the following method: Pregnant rats were put in anesthesia using intraperitoneal injection of trichloroacetaldehyde (200 mg/kg). The calvaria of the fetal rats were then dissected with aseptic technique. Soft tissues were removed under a dissecting microscope. The calvaria were divided into small pieces and then treated with 0.1% collagenase (Sigma Chemical, St. Louis, Mo.) solution for 10 minutes at 37° C. The cells released from the calvariae by two 20-minute sequential collagenase digestions were pooled and filtered through 70 μm nylon filters (Falcon, BD BioSciences, San Jose, Calif.). The cells were then grown on plastic cell culture dishes in 95:5 air-$CO_2$ with Dulbecco's modified Eagle's medium (DMEM) (Gibco, Grand Island, N.Y.) which was supplemented with 20 mM HEPES and 10% heat-inactivated FCS, 2 mM-glutamine, penicillin (100 U/ml) and streptomycin (100 μg/ml) (pH adjusted to 7.6). The cell medium was changed twice a week. Osteoblasts were confirmed by morphology and expression of alkaline phosphatase (ALP). To examine the maturation of osteoblasts, cells were cultured for up to 14 days in a growth medium containing ascorbic acid (50 μg/ml) (Sigma Chemical, St. Louis, Mo.) and β-glycerophosphate (10 mM) (Sigma Chemical, St. Louis, Mo.) and the medium was changed every 3 day.

Assay of alkalinephosphatase activity: Cells cultured in 6-well plates in the presence or absence of Indazole 1 were harvested in 1 ml of 0.2% Nonidet P-40 and cell suspension was disrupted by sonication. After centrifugation at 1500 g for 5 min, ALP activity in the supernatant was measured by the method of Lowry et al (1954) *J Biol Chem* 207:19–37.

von Kossa staining: Osteoblasts were cultured in DMEM containing 50 μg/ml vitamin C and 10 mM β-glycerophosphate for 2 weeks and the medium was changed every 3 days. To examine nodule formation, the cells were fixed in 4% paraformaldehyde for 10 min, rinsed with water, stained with 1% silver nitrate, placed under a UV lamp for 30 min and rinsed with water before treating with 5% sodium thiosulfate for 2 min. The cells were then washed twice with water and counterstained with 1% Safranin-O to visualize the matrix. The number of nodules formed per well was counted under a light microscope. Collagen synthesis was determined by measuring the 4-hydroxyproline content in cultured osteoblasts. Cells cultured in DMEM containing 50 μg/ml vitamin C and 10 mM β-glycerophosphate for 2 weeks were hydrolyzed in 6N HCl for 16 h at 116° C. After lyophilizing and reconstituting a lysate in distilled water, the amount of 4-hydroxyproline was determined by spectrophotometry at 550 nm as described by Berg (1982) *Meth Enzymol.* 82: 372–398.

Assay of cell proliferation: Osteoblasts ($2\times10^4$ cells/well) were seeded on 24-well plates (Costar, Cambridge, Mass.). The cells were incubated in a serum-free medium for 24 hr before addition of Indazole 1. After incubation with Indazole 1 for 24 hr, BrdU at 10 μM was applied for another 24 hr incubation. BrdU incorporation was assayed according to the protocol of enzyme-linked immunosorbent assay chemiluminescence detection kit (Roche Molecular Biochemicals) using a luminescence counter (TopCount; Packard Instruments, Meriden, Conn.). The counts per second correlate directly to the amount of DNA synthesis and hereby the number of proliferating cells.

Osteoclastogenesis: Bone marrow cells were prepared by removing femurs from 6–8-week-old SD rats and flushing the bone marrow cavity with DMEM which was supplemented with 20 mM HEPES and 10% heat-inactivated FCS, 2 mM-glutamine, penicillin (100 U/ml) and streptomycin (100 μg/ml). After 24 hr, the non-adherent cells (hematopoietic cells) were collected and used as osteoclast precursors. The cells were seeded at $1\times10^6$ cells/well (0.5 ml) in 24-well plates in the presence of human recombinant soluble RANKL (50 ng/ml, Peprotech EC Ltd., London, United Kingdom) and murine M-CSF (20 ng/ml, Genzyme, Cambridge, Mass.). The culture medium was changed every 3 days. After 8~10 days, osteoclast formation was confirmed by an assay of tartrate-resistant acid phosphatase (TRAP) (Kotake et al., 1999). In brief, the adherent cells were fixed with 10% formaldehyde in phosphate-buffered saline for 3 min. After treatment with ethanol/acetone (50:50 v/v) for 1 min, the cell surface was air dried and incubated for 10 min at room temperature in an acetate buffer (0.1 M sodium acetate, pH 5.0) containing 0.01% naphthol AS-MX phosphate (Sigma) and 0.03% fast red violet LB salt (Sigmna) in the presence of 50 mM sodium tartrate. Osteoclast-like TRAP-positive cells in each well were scored by counting the number of TRAP-positive and multinucleated cells containing more than three nuclei.

Assay of bone resorption of osteoclast: Osteoclast precursors were isolated from rat long bones as mentioned above. The cells were re-suspended in a complete DMEM medium and plated into a calcium phosphate apatite-coated 24-well plate, OAAS (Oscotec, OCT USA Inc.) at $1\times10^6$ cells/0.5 ml/well. The cells were cultured for 5 days in the presence of M-CSF (20 ng/ml) plus sRANKL (50 ng/ml). Indazole 1 was injected daily for additional 3 days in the absence of M-CSF and sRANKL. Culture was terminated on day 8 and the remaining cells in the plate were lysed using 1 N NaOH. Five images per well were obtained using an inverted microscope (200×), and resorbed area was measured using an image analyzer. Local injection Male SD rats weighing 70–88 gm were used. Implantation of a cannula (22G) was done from the posteriolateral side into the proximal tibial metaphysis in both limbs of rats anesthetized with pentobarbital. The cannula had its outer end in the subcutaneous tissue. Indazole 1 was percutaneously injected through the cannula into the proximal tibia once/day for 1 week. The same concentration of DMSO diluted with normal saline was injected into the right side for comparison. On day 14, the rats were sacrificed and tibiae were fixed in 10% formaldehyde for 48 h at 4° C.

Bone histomorphometry: After formalin fixation of tibia was completed, the tibiae were then decalcified in 0.5 N hydrochloric acid, dehydrated in an ascending series of ethanol solution and acetone, and embedded in paraffin. Serial sections (5 μm) were cut longitudinally and stained with Mayer's hematoxylin-eosin solution (Yang et al. (1993) *Calcif Tissue Int* 52:57–61). Images of the growth plate and proximal tibia were photographed using a photoMicro-Graphic Digitize integrate System (MGDS; Total-Integra Technology Co., Ltd., Taipei, Taiwan). Bone volume measurements were performed on the whole secondary spongiosa, which is located under the primary spongiosa and characterized by a network of larger trabeculae. Bone volumes were calculated using an image analysis software. All measurements were done in a single-blind fashion.

Ovariectomy and cut of sciatic nerve: Ovariectomy and cut of sciatic nerve were performed in adult female and male rats (3 month-old), respectively. After surgery, the rats were injected with Indazole 1 (i.p., 1 mg/Kg) or a vehicle daily for 4 weeks. On the day following the last injection, the rats were sacrificed and their tibia and femur were removed.

Tibia and femur Preparation: At the end of the program, the rats were sacrificed by decapitation. The tibiae were removed, cleaned of soft tissue, and the length of the tibia was measured with a precision caliper (±0.05 mm) as described by Weinreb et al. (1991) *J Bone Miner Res* 6:725–731. The tibiae were fixed in 10% formaldehyde for 48 h at 4° C. for bone histomorphometry analysis. Some of the tibia and femur were also removed and kept at −20° C. for bone mineral analysis.

Analysis of bone mineral density (BMD) and content (BMC): BMD and BMC of the tibia and femur were measured with a dual-energy X-ray absorptiometer (DEXA, XR-26; Norland, Fort Atkinson, Wis.). The mode adapted to the measurements of small subjects was adopted. A coefficient of variation of 0.7% was calculated from daily measurements of BMD on a lumbar phantom for more than 1 year (Yang et al. (1998) *Calcif Tissue Int* 63:86–90). The tibia and femur were thawed to room temperature before bone mineral analysis. The whole tibiae and femur were scanned and BMD and BMC were measured by absorptiometer.

Biomechanical three-point bending test: Mechanical properties of bone tissues were measured via a three-point bending test using a MTS-858 testing machine (MTS System Inc., Minneapolis, Minn.). The span of two support points was 20 millimeters and the deformation rate was 1 mm/min. Load/deformation curves were acquired by Team 490 software (version 4.10, Nicolet Instrument Technologies Inc., Madison, Wis.). Sigma Plot 6.0 software (SPSS Inc., Chicago, Ill.) was used to calculate extrinsic material properties of bone samples, including maximal load, ultimate load, energy to maximal load, energy to ultimate load, and linear stiffness. Energy to maximal load and energy to ultimate load were calculated as the areas under the load/deforming curves. Stiffness was calculated as the slope of the linear portion of the load/deformation curves. The cross-sectional moment of inertia was calculated under the assumption that the cross-sections were elliptically shaped (Turner et al., The effects of fluoridated water on bone strength. *Orthop Res* (1992) 10: 581–587).

Maximal stress, ultimate stress, and elastic modulus (Young's modulus) were calculated using the methods described in Turner et al., Basic biomechanical measurements of bone: a tutorial, *Bone* (1993) 14:595–608.

Results

Bone growth: Male young rats (SD) weighing 70–90 gm were divided into six groups. The average weight of the rats in each group was 73.9±1.1 gm. Indazole 1 was dissolved in DMSO and diluted with saline to a final concentration of 10 μM. One of the six groups was a control group, and the other groups were punctuated with a needle cannula alone, injected with a vehicle using a needle cannula (day 1, once), injected with Indazole 1 (day 1, once), injected with a vehicle using a needle cannula (days 1–7, daily), and injected with Indazole 1 (days 1–7, daily), respectively. Punctuation of a needle cannula (22G) alone or injection of a vehicle using a needle cannula did not affect the bone volume when the rats were sacrificed after 14 days. However, the bone volume of the secondary spongiosa significantly increased after the rats were injected with Indazole 1 (0.1 nmole) for 7 days and then fed for additional 7 days. Trabecular bone in the secondary spongiosa increased by 90% after local injection of Indazole 1 for 7 days. The tibia length was not significantly affected by local injection of Indazole 1 (tibia length: 3.31±0.01 cm for control, and 3.32±0.02 cm, for Indazole 1-treated group, n=9).

Male young rats were injected with Indazole alone, or injected with Indazole 1 and $N^G$-nitro-L-arginine-methyl-ester (L-NAME, 0.6 nmole/day), a NO synthase (NOS) inhibitor. In comparison with Indazole 1 alone, concomitant administration of Indazole 1 and L-NAME significantly attenuated the enhancement effect of Indazole 1 on the bone formation in the secondary spongiosa.

Prevention of bone loss: Ovariectomy (OVX) was performed in adult female rats (n=28). After ovariectomy, one group of the ovariectomized rats (n=16) were injected with Indazole 1 (i.p., 1 mg/kg/day), and the other group (n=12) were not. 15 un-ovarietctomized adult female rats were used as sham-operated controls and were not injected with Indazole 1. Ovariectomy did not significantly affect the length and weight of both tibia and femur, but reduced bone mineral density (BMD) and content (BMC) in both femur and tibia. See Table 1 below. Unexpectedly, daily injection of Indazole 1 provided protection against ovariectomy-induced loss of BMD and BMC in both tibia and femur. In comparison with sham controls, ovariectomy resulted in a reduction in trabecular bone of tibia secondary spongiosa. A 60% reduction in bone volume was observed 4 weeks after ovariectomy. On the other hand, daily injection of Indazole 1 (1 mg/kg) for 4 weeks reduced loss of trabecular bone. The bone volume reached 76% of sham-operated controls.

TABLE 1

Effect of Indazole 1 on the bone mineral density and content

|  | sham-operated (n = 15) | OVX (n = 12) | OVX + Indazole 1 (n = 16) |
|---|---|---|---|
| Tibia length (cm) | 3.97 ± 0.02 | 4.00 ± 0.02 | 4.05 ± 0.03 |
| Femur length (cm) | 3.51 ± 0.01 | 3.55 ± 0.01 | 3.55 ± 0.01 |
| Tibia weight (g) | 0.67 ± 0.02 | 0.67 ± 0.02 | 0.67 ± 0.01 |
| Femur weight (g) | 0.86 ± 0.01 | 0.87 ± 0.02 | 0.87 ± 0.01 |
| Tibia BMD | 0.098 ± 0.002 | 0.087 ± 0.001[a] | 0.097 ± 0.002[b] |
| Tibia BMC | 0.194 ± 0.012 | 0.145 ± 0.011[a] | 0.173 ± 0.011[b] |
| Femur BMD | 0.116 ± 0.002 | 0.097 ± 0.004[a] | 0.112 ± 0.002[b] |
| Femur BMC | 0.302 ± 0.001 | 0.225 ± 0.001[a] | 0.281 ± 0.001[b] |

Indazole 1 was daily administered by i.p. injection (1 mg/kg) for 1 month following the day of ovariectomy in adult female rats. The control group was given the vehicle (3% DMSO, 0.3 ml).
[a]$p < 0.05$ compared with sham-operated group.
[b]$p < 0.05$ compared with OVX group.
BMD: bone mineral density
BMC: bone mineral content
Data are presented as mean ± S.E.

A three-point bending test was conducted in femurs. Compared with sham-operated controls, the OVX rats showed significantly lower ultimate stress and Young's modulus of femurs. Unexpectedly, the Indazole 1-treated OVX rats had only slightly lower ultimate stress and Young's modulus of femurs. See Table 2 below:

TABLE 2

Biomechanical properties of femurs

| | sham-operated (n = 15) | OVX (n = 12) | OVX + Indazole 1 (n = 16) |
|---|---|---|---|
| Maximal load, N | 103.4 ± 3.6 | 90.2 ± 5.3* | 100.5 ± 3.0§ |
| Ultimate load, N | 82.5 ± 6.1 | 70.1 ± 7.0* | 79.8 ± 3.3§ |
| Young's modulus, GPa | 201 ± 6.5 | 178 ± 5.8* | 193 ± 7.1§ |
| Ultimate stress, Mpa | 15.1 ± 1.5 | 12.3 ± 2.2* | 14.6 ± 2.5§ |

Indazole 1 was daily administered by i.p. injection (1 mg/kg) for 4 weeks following the day of ovariectomy in adult female rats. The control group was given with vehicle (3% DMSO, 0.3 ml)
*P < 0.05 as compared with sham-operated controls,
§P < 0.05 as compared with OVX-group.

Cut of sciatic nerve was performed in adult male rats. The results are shown in Table 2 below. In comparison with the contralateral side, the length of both tibia and femur in surgery side did not significantly change 1 month after sciatic nerve section. However, the weight, BMD, BMC and bone volume of both tibia and femur decreased in response to the cut of sciatic nerve. Unexpectedly, daily injection of Indazole1 (1 mg/kg) immediately after the cut of sciatic nerve for 4 weeks antagonized the bone loss induced by nerve section. See Table 3 below:

TABLE 3

Prevention by Indazole 1 of bone loss induced by the cut of sciatic nerve

| | Control | | Indazole 1 treatment | |
|---|---|---|---|---|
| | Surgery side | Contralateral side | Surgery side | Contralateral side |
| Tibia length (cm) | 4.34 ± 0.01 | 4.35 ± 0.01 | 4.35 ± 0.01 | 4.36 ± 0.01 |
| Femur length (cm) | 3.95 ± 0.01 | 3.95 ± 0.01 | 3.96 ± 0.01 | 3.95 ± 0.02 |
| Tibia weight (g) | 0.87 ± 0.01[a] | 0.96 ± 0.02 | 0.91 ± 0.03 | 0.92 ± 0.03 |
| Femur weight (g) | 1.12 ± 0.02[a] | 1.18 ± 0.01 | 1.17 ± 0.03 | 1.16 ± 0.03 |
| Tibia BMD | 0.106 ± 0.001[a] | 0.113 ± 0.002 | 0.106 ± 0.002 | 0.106 ± 0.002 |
| Tibia BMC | 0.288 ± 0.007[a] | 0.311 ± 0.007 | 0.298 ± 0.014 | 0.282 ± 0.013 |
| Femur BMD | 0.125 ± 0.003[a] | 0.134 ± 0.003 | 0.129 ± 0.003 | 0.132 ± 0.003 |
| Femur BMC | 0.386 ± 0.011[a] | 0.425 ± 0.013 | 0.394 ± 0.015 | 0.419 ± 0.016 |
| Bone volume (%) | 5.93 ± 0.80[ab] | 13.3 ± 1.18 | 9.43 ± 0.8 | 11.9 ± 0.98 |

Indazole 1 was daily administered by i.p. injection (1 mg/kg) for 1 month following the day of sciatic nerve section in adult male rats. The control group was given the vehicle (3% DMSO, 0.3 ml). Data are presented as mean ± S.E. (n = 14 for control and n = 10 for Indazole 1-treated group).

Effects on cultured osteoblasts: The effect of chronic treatment of Indazole 1 on the activity of alkaline phosphatase was examined. Osteoblasts were cultured according to the method of primary osteoblast cultures, and treated with Indazole 1 (10 μM) for 2 weeks. The treatment significantly increased ALP activity as shown by ALP staining. The increase of ALP activity by Indazole 1 was concentration-dependent and antagonized by L-NAME (60 μM), ODQ (20 μM) or KT5823 (2 μM). The effect of Indazole 1 on in vitro formation of bone nodules was also examined. It was found that mineralized nodules were formed when osteoblasts were cultured in a medium containing vitamin C and β-glycerophosphate. The mineralized nodules revealed a bone structure with active osteoblasts, entrapped osteocytes, extracellular collagen fibrils and hydroxyapatite deposits under electron microscopy, making this system a valid model to study bone formation in vitro. Unexpectedly, treatment with Indazole 1 for 2 weeks increased the number of bone nodules in a concentration-dependent manner (bone nodules were observed by von Kossa staining). Indazole 1 at 0.1 and 1 μM slightly increased the proliferation of osteoblasts (119.3% and 126.1% of control, respectively).

Fibronectin (Fn) plays an important role in the regulation of adhesion, migration, and maturation of osteoblasts. Fn fibrillogenesis is involved in the process of bone mineralization. The effect of Indazole 1 on Fn fibrillogenesis in cultured osteoblasts was examined. The immobilized form of fibrillogenesis from the endogenously released Fn by monolayer Day 3~5 osteoblasts was studied using immunocytochemistry. Incubation of Day-3 osteoblasts with Indazole 1 (10 μM) for 24 hr increased extracellular Fn assembly. Flow cytometry was used to analyze the effect of Indazole 1 on the surface expression of α5 and β1 integrins. Unexpectedly, it was found that Indazole 1 treatment for 24 hr increased the cell surface expression of both integrins. On the other hand, the collagen synthesis was increased by Indazole 1 only at a higher concentration of 10 μM.

Effect on differentiation and activation of osteoclasts: Cultures of osteoclast precursors in the presence of M-CSF (20 ng/ml) and sRANKL (50 ng/ml) for 8 days induced the formation of large mature osteoclasts with multi-nuclei characterized by acquisition of mature phenotypic markers, e.g., TRAP. Indazole 1, unexpectedly, inhibited the differentiation of osteoclast in a concentration-dependent manner.

The effect of Indazole 1 on resorption activity of osteoclasts was also examined. Osteoclast precursors were cultured in the presence of M-CSF and sRANKL for 5 days, and then M-CSF and sRANKL were removed from the medium on an osteoclasts activity assay substrate plate. Different concentrations of Indazole 1 were added to the medium for additional 3-day incubation. In comparison with a control, Indazole 1 significantly inhibited resorption activity of osteoclasts in a concentration-dependent manner.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, a compound structurally analogous to a fused pyrazolyl compound can also be used to practice the present invention. Thus, other embodiments are also within the claims.

What is claimed is:

1. A method for increasing bone density, comprising administering to a subject in need thereof an amount of a compound effective for increasing bone density, wherein said compound is a compound of the formula:

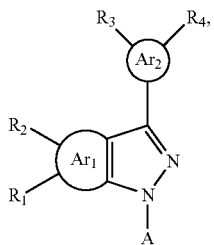

wherein,

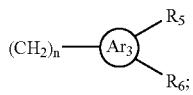

A is $Ar_1$ is phenyl, $Ar_2$ is 5'-furyl, $Ar_3$ is phenyl and n is 1; each of $R_1$, $R_2$, $R_3$, $R_4$, $R_5$, and $R_6$, independently, is H, nitro, halogen, R, OH, OR, C(O)OH, C(O)OR, C(O)SH, C(O)SR, C(O)NH$_2$, C(O)NHR, C(O)NRR', ROH, ROR', RSH, RSR', ROC(O)R'OH, NHR, NRR', RNHR', or RNR'R''; or $R_1$ and $R_2$ together, $R_3$ and $R_4$ together, or $R_5$ and $R_6$ together are ORO; wherein each of R, R', and R'', independently is $C_1$–$C_6$ alkyl; and wherein said subject has osteoporosis, bone fracture, failed arthrodesis, dyschondroplasia, achondroplasia or congenital pseudoarthrosis.

2. The method of claim 1, wherein one of $R_3$ and $R_4$ is substituted at position 2 of 5'-furyl.

3. The method of claim 2, wherein each of $R_1$, $R_2$, $R_5$ and $R_6$ is H.

4. The method of claim 3, wherein one of $R_3$ and $R_4$ is CH$_2$NHCH$_3$, CH$_2$OCH$_3$, or COOCH$_3$.

5. The method of claim 3, wherein one of $R_3$ and $R_4$ is H, and the other is CH$_2$OH.

6. A method for treating osteoporosis, comprising administering to a subject in need thereof an amount of a compound effective for treating osteoporosis, wherein said compound is a compound of the formula:

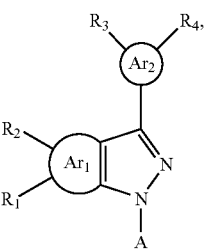

wherein,

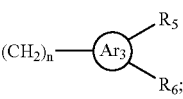

A is $Ar_1$ is phenyl, $Ar_2$ is 5'-furyl, $Ar_3$ is phenyl and n is 1; each of $R_1$, $R_2$, $R_3$, $R_4$, $R_5$, and $R_6$, independently, is H, nitro, halogen, R, OH, OR, C(O)OH, C(O)OR, C(O)SH, C(O)SR, C(O)NH$_2$, C(O)NHR, C(O)NRR', ROH, ROR', RSH, RSR', ROC(O)R'OH, NHR, NRR', RNHR', or RNR'R''; or $R_1$ and $R_2$ together, $R_3$ and $R_4$ together, or $R_5$ and $R_6$ together are ORO; wherein each of R, R', and R'', independently is $C_1$–$C_6$ alkyl.

7. The method of claim 6, wherein one of $R_3$ and $R_4$ is substituted at position 2 of 5'-furyl.

8. The method of claim 7, wherein each of $R_1$, $R_2$, $R_5$ and $R_6$ is H.

9. The method of claim 8, wherein one of $R_3$ and $R_4$ is H, and the other is CH$_2$NHCH$_3$, CH$_2$OCH$_3$, or COOCH$_3$.

10. The method of claim 8, wherein one of $R_3$ and $R_4$ is H, and the other is CH$_2$OH.

* * * * *

UNITED STATES PATENT AND TRADEMARK OFFICE
CERTIFICATE OF CORRECTION

PATENT NO. : 7,160,916 B2 Page 1 of 1
APPLICATION NO. : 10/932323
DATED : January 9, 2007
INVENTOR(S) : Wen-Mei Fu et al.

It is certified that error appears in the above-identified patent and that said Letters Patent is hereby corrected as shown below:

In the Claims:

Column 11, lines 26-33, delete

"  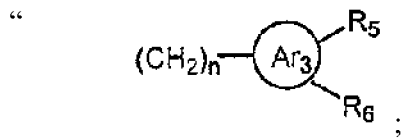 ;

A is $Ar_1$ is phenyl, $Ar_2$ is 5'-furyl, $Ar_3$ is phenyl and n is 1;"

and insert

-- A is 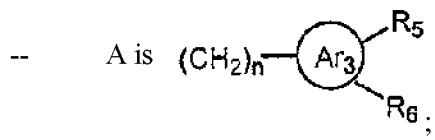 ;

$Ar_1$ is phenyl, $Ar_2$ is 5'furyl, $Ar_3$ is phenyl and n is 1;--

Signed and Sealed this

Eleventh Day of December, 2007

JON W. DUDAS
*Director of the United States Patent and Trademark Office*